US011647133B2

(12) United States Patent
Kubota et al.

(10) Patent No.: US 11,647,133 B2
(45) Date of Patent: May 9, 2023

(54) INFORMATION PROCESSING APPARATUS AND METHOD FOR CONTROLLING INFORMATION PROCESSING APPARATUS

(71) Applicant: CANON KABUSHIKI KAISHA, Tokyo (JP)

(72) Inventors: Tsutomu Kubota, Chiba (JP); Motoki Koshigaya, Saitama (JP); Tatsuya Ogawa, Ibaraki (JP); Hidetaka Tabuchi, Chiba (JP); Tsunahito Nakashita, Chiba (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/462,596

(22) Filed: Aug. 31, 2021

(65) Prior Publication Data
US 2022/0078290 A1    Mar. 10, 2022

(30) Foreign Application Priority Data
Sep. 9, 2020    (JP) .............................. JP2020-151318

(51) Int. Cl.
*G06F 15/00*     (2006.01)
*H04N 1/00*      (2006.01)
*H04N 1/44*      (2006.01)
*A61L 2/18*      (2006.01)

(52) U.S. Cl.
CPC ......... *H04N 1/0049* (2013.01); *H04N 1/0097* (2013.01); *H04N 1/00411* (2013.01); *H04N 1/00472* (2013.01); *H04N 1/4406* (2013.01); *A61L 2/18* (2013.01)

(58) Field of Classification Search
CPC ............. H04N 1/0049; H04N 1/00411; H04N 1/00472; H04N 1/0097; H04N 1/4406
USPC ....................................................... 358/1.15
See application file for complete search history.

(56) References Cited

U.S. PATENT DOCUMENTS

| | | | |
|---|---|---|---|
| 2017/0346980 A1* | 11/2017 | Nishimura | ......... G03G 15/0225 |
| 2018/0244063 A1* | 8/2018 | Okumura | ............. B41J 2/17553 |
| 2019/0361600 A1* | 11/2019 | Matsuda | ............... G06F 1/3215 |
| 2022/0057906 A1* | 2/2022 | Schmied | .................. A61B 8/54 |

FOREIGN PATENT DOCUMENTS

JP     2000347723 A    12/2000

\* cited by examiner

*Primary Examiner* — Mark R Milia
(74) *Attorney, Agent, or Firm* — Canon U.S.A., Inc. IP Division

(57) ABSTRACT

An apparatus includes a notification unit configured to notify a user of information, and a controller configured to identify at least one unit based on an operation performed by the user among a plurality of units included in the apparatus, wherein the notification unit can notify the user of first information indicating the identified at least one unit and second information regarding disinfection of the identified at least one unit.

19 Claims, 16 Drawing Sheets

FIG.14

TABLE FOR LEVEL = LOW

| OPERATION EXAMPLE 1 | TIME | MODE | USER | OPERATION | INPUT DETECTED |
|---|---|---|---|---|---|
| 1-1 | 10:21:11 | LOGIN | A | | TOUCH PANEL |
| 1-2 | 10:21:40 | NORMAL OPERATION | A | COPY | TOUCH PANEL |
| 1-3 | 10:21:50 | NORMAL OPERATION | A | COPY | NUMERICAL KEYPAD |
| 1-4 | 10:35:50 | LOGIN | B | | TOUCH PANEL |
| 1-5 | 10:36:05 | NORMAL OPERATION | B | SCAN AND TRANSMIT | TOUCH PANEL |
| 1-6 | 11:40:05 | CLEANING (PANEL) | | | TOUCH PANEL |
| 1-7 | 14:11:23 | LOGIN | C | | TOUCH PANEL |
| 1-8 | 14:11:40 | NORMAL OPERATION | C | COPY | TOUCH PANEL |
| 1-9 | 14:11:50 | NORMAL OPERATION | C | COPY | NUMERICAL KEYPAD |
| 1-10 | 14:12:20 | NORMAL OPERATION | C | COPY | SHEET FEEDING TRAY 1 |

FIG.15

TABLE FOR LEVEL = HIGH

| OPERATION EXAMPLE 2 | TIME | MODE | USER | OPERATION | INPUT DETECTED |
|---|---|---|---|---|---|
| 2-1 | 10:21:11 | LOGIN | A | | TOUCH PANEL |
| 2-2 | 10:21:40 | CLEANING | A | | TOUCH PANEL |
| 2-3 | 10:22:01 | NORMAL OPERATION | A | COPY | TOUCH PANEL |
| 2-4 | 10:22:15 | NORMAL OPERATION | A | COPY | NUMERICAL KEYPAD |
| 2-5 | 10:35:30 | LOGIN | A | | TOUCH PANEL |
| 2-6 | 10:35:50 | CLEANING | A | | TOUCH PANEL |
| 2-7 | 10:36:05 | NORMAL OPERATION | A | SCAN | TOUCH PANEL |
| 2-8 | 14:11:10 | LOGIN | C | | TOUCH PANEL |
| 2-9 | 14:11:23 | CLEANING | C | | TOUCH PANEL |
| 2-10 | 14:11:50 | NORMAL OPERATION | C | COPY | TOUCH PANEL |
| 2-11 | 14:12:30 | NORMAL OPERATION | C | COPY | SHEET FEEDING TRAY 1 |

FIG. 16

TABLE FOR LEVEL = INTERMEDIATE

| OPERATION EXAMPLE 3 | TIME | MODE | USER | OPERATION | INPUT DETECTED |
|---|---|---|---|---|---|
| 3-1 | 10:21:11 | LOGIN | A | | TOUCH PANEL |
| 3-2 | 10:21:40 | CLEANING | A | | TOUCH PANEL |
| 3-3 | 10:22:01 | NORMAL OPERATION | A | COPY | TOUCH PANEL |
| 3-4 | 10:22:15 | NORMAL OPERATION | A | COPY | NUMERICAL KEYPAD |
| 3-5 | 10:35:30 | LOGIN | A | | TOUCH PANEL |
| 3-6 | 10:35:50 | NORMAL OPERATION | A | COPY | TOUCH PANEL |
| 3-7 | 10:36:05 | NORMAL OPERATION | A | SCAN AND TRANSMIT | TOUCH PANEL |
| 3-8 | 14:11:10 | LOGIN | C | | TOUCH PANEL |
| 3-9 | 14:11:23 | CLEANING | C | | TOUCH PANEL |
| 3-10 | 14:11:50 | NORMAL OPERATION | C | COPY | TOUCH PANEL |
| 3-11 | 14:12:30 | NORMAL OPERATION | C | COPY | SHEET FEEDING TRAY 1 |

INFORMATION PROCESSING APPARATUS AND METHOD FOR CONTROLLING INFORMATION PROCESSING APPARATUS

BACKGROUND OF THE DISCLOSURE

Field of the Disclosure

The aspect of the embodiments relates to an information processing apparatus and a method for controlling an information processing apparatus.

Description of the Related Art

In recent years, due to the enhanced mobility of people and goods, a phenomenon has started to be seen in which, when a new virus or a mutated virus has broken out, the virus has spread all over the world instantaneously and created a large number of infected people. It is known that, for most of these infections, people are infected therewith by introducing the virus contained in an airborne droplet flying from an infected person into their body. Then, there is also reported a study result indicating that these viruses can stay in an infectious state for days on a glass or plastic surface or the like. It is known that these viruses can be deactivated even with ethanol, which is a conventionally known disinfectant.

Multi function peripherals (MFPs) (hereinafter abbreviated as MFPs), which are image forming apparatuses, are used in such a manner that one apparatus is shared by a large number of users unlike personal computers (PCs). Plastic or glass parts are used for the exteriors thereof. Therefore, the MFPs involve such a risk that the MFPs may serve as an infection route and undesirably cause the spread of an infection when a virus is attached to the MFPs as described above.

Similar concern has also been posed for a while regarding ticket machines and automatic teller machine (ATM) apparatuses placed in town and used in such a manner that the same machine has been shared by many and unspecified people. For a touch panel provided to operate such an apparatus, it is difficult to automatically determine whether a touch is intended to operate the apparatus or is intended to wipe the surface for cleaning. As a method for solving this issue, for example, Japanese Patent Application Laid-Open No. 2000-347723 discusses a proposal that allows a touch panel to be cleaned by switching a screen mode to a cleaning mode, displaying a turn-off button during the cleaning mode, and disabling an input other than a touch onto the turn-off button.

However, the touch panel is not the only member that users touch when using the information processing apparatus. Therefore, a user using the information processing apparatus has no idea about which member in the information processing apparatus should be disinfected when attempting disinfection.

SUMMARY OF THE DISCLOSURE

The aspect of the embodiments is directed to an apparatus including a notification unit configured to notify a user of information, and a controller configured to identify at least one unit based on an operation performed by the user among a plurality of units included in the apparatus, wherein the notification unit can notify the user of first information indicating the identified at least one unit and second information regarding disinfection of the identified at least one unit.

Further, the aspect of the embodiments allows the user using the information processing apparatus to understand which member in the information processing apparatus should be disinfected.

Further features of the disclosure will become apparent from the following description of exemplary embodiments with reference to the attached drawings.

BRIEF DESCRIPTION OF THE DRAWINGS

FIG. 14 illustrates an example of a table indicating an operation history when the cleaning level is low.

FIG. 15 illustrates an example of a table indicating an operation history when the cleaning level is high.

FIG. 16 illustrates an example of a table indicating an operation history when the cleaning level is intermediate.

DESCRIPTION OF THE EMBODIMENTS

Each exemplary embodiment of the disclosure will be described in detail with reference to the accompanying drawings. However, the exemplary embodiment that will be described below does not limit the disclosure defined according to the claims, and, further, not all of combinations of features that will be described in each exemplary embodiment are necessarily essential to a solution of the disclosure. In the present exemplary embodiment, an image forming apparatus will be described as an example of an information processing apparatus.

Figure 1:
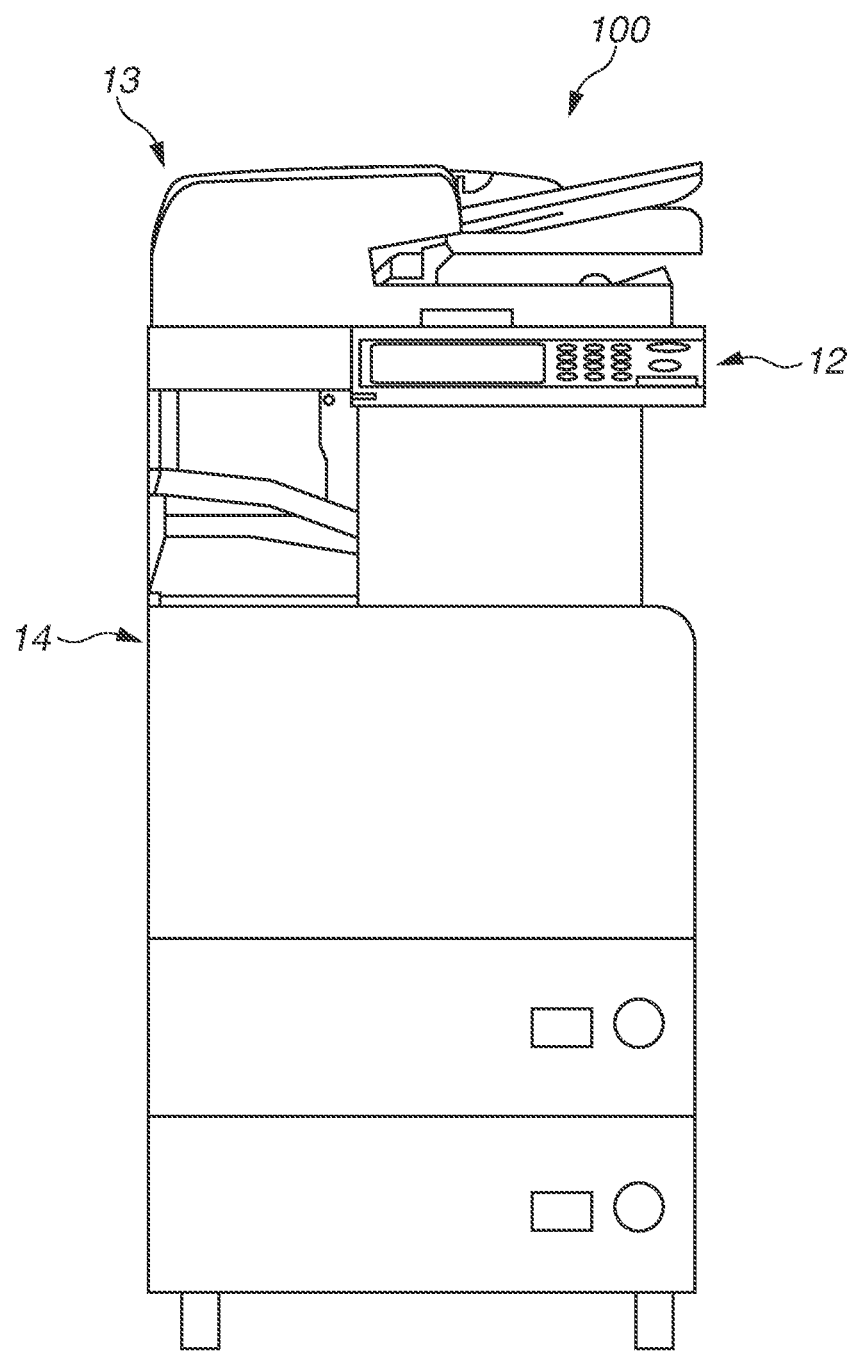
FIG. 1 illustrates the external appearance of the front side of an image forming apparatus.
Figure 2:
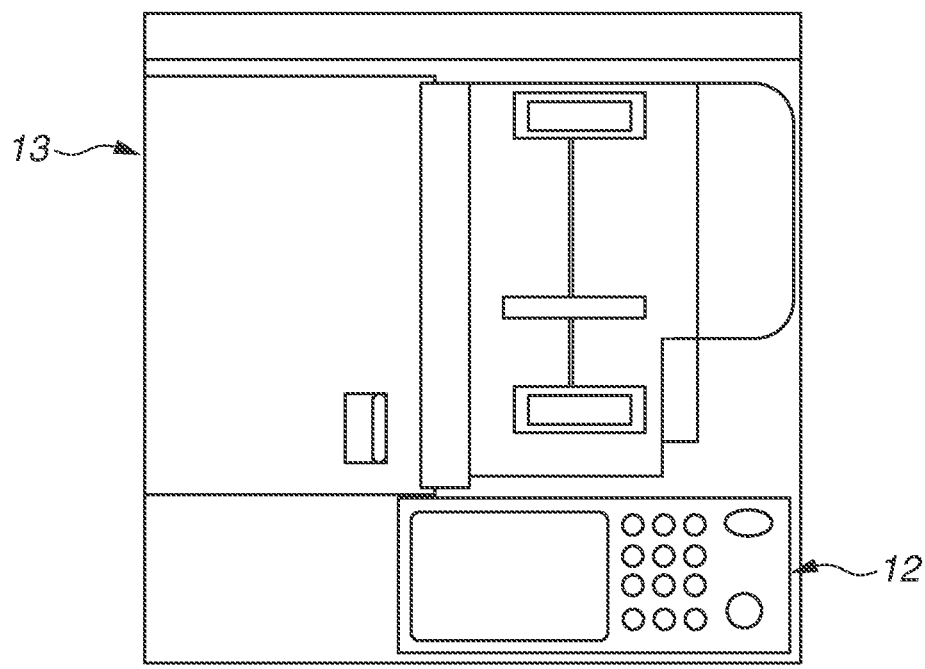
FIG. 2 illustrates the image forming apparatus as viewed from above.

FIG. 1 illustrates the external appearance of an image forming apparatus 100 according to a first exemplary embodiment, and FIG. 2 illustrates the image forming apparatus 100 according to the first exemplary embodiment as viewed from above. The image forming apparatus 100 includes a printer unit 14, a scanner unit 13, and a display unit 12, and has a plurality of functions, such as a print function, a scanner function, a copy function, and a facsimile (FAX) function. The printer unit 14 includes an internal configuration including a drum and the like, and members including a sheet feeding tray that holds a sheet for use in printing and a discharge tray to which a printed sheet is discharged. The scanner unit 13 includes at least members such as a platen glass on which a document is placed and a pressing plate that sandwiches the document placed on the platen glass. The pressing plate may be an automatic document feeder (ADF).

The image forming apparatus 100 can collaborate with a mobile terminal via, for example, Bluetooth communication or contact communication, although this is not illustrated. Further, an externally attached controller may be provided to the image forming apparatus 100 via a wiring. Further, a finisher that performs post-processing (for example, stapling and punching) on a printout of the image forming apparatus 100 may be disposed. In this case, the finisher also serves as the sheet discharge tray.

Figure 3:
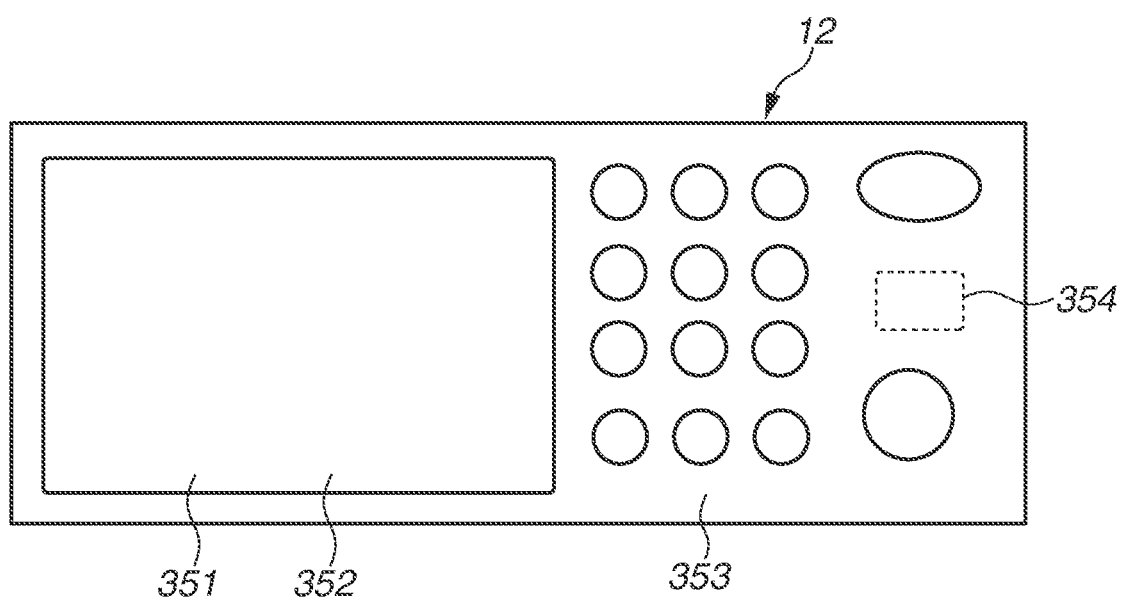
FIG. 3 illustrates the external appearance of a display unit.

FIG. 3 illustrates the external appearance of the display unit 12. A liquid crystal display (LCD) 351 is a display for displaying an image. A touch panel 352 is a film overlaid on the top surface of the LCD 351 and having a sensor function for outputting an X-Y coordinate position of a touch input of a user. A numerical keypad unit 353 receives a key input. Then, a card reader 354 reads an identification (ID) card for identifying the user.

Figure 4:
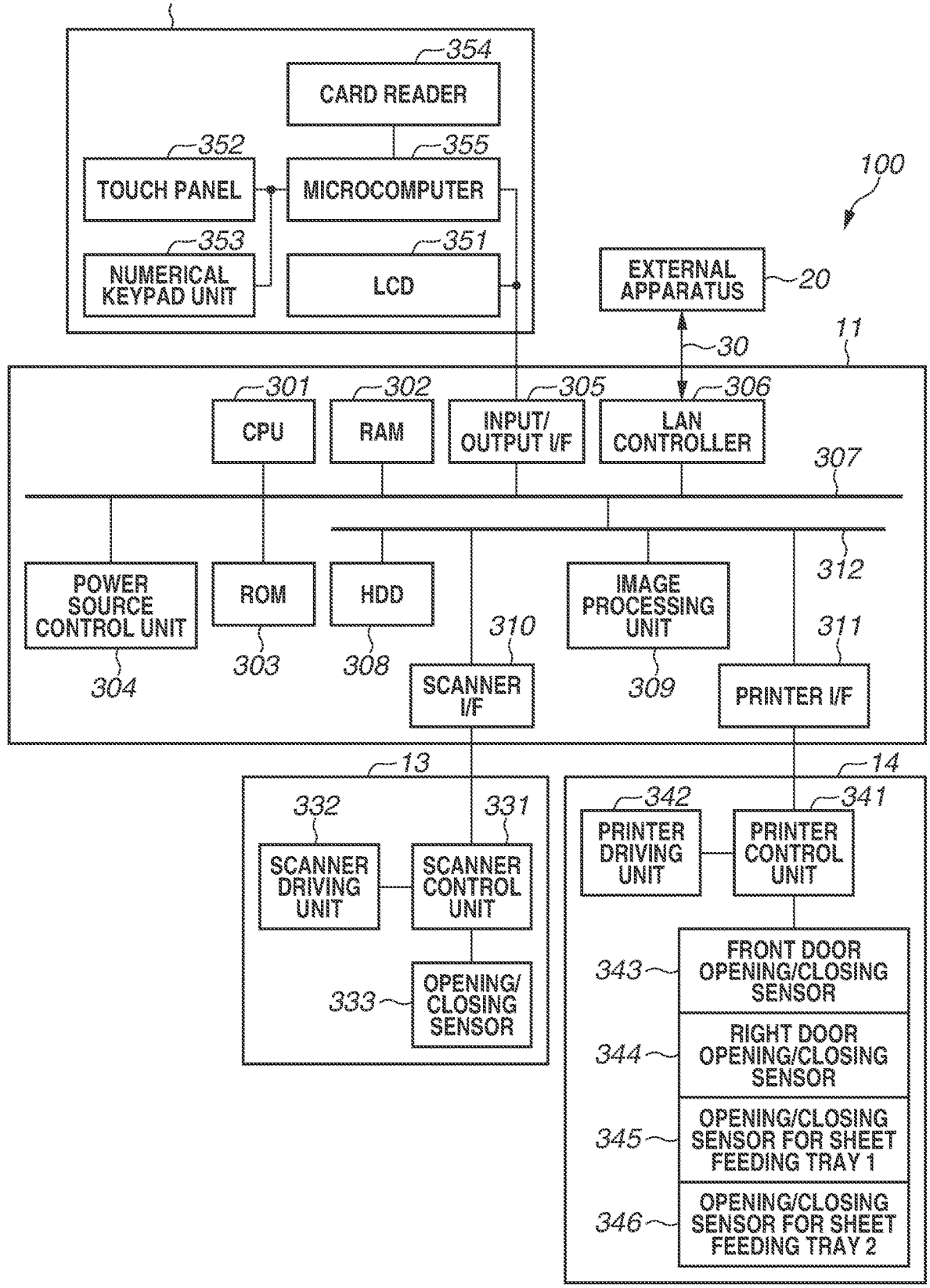
FIG. 4 is a hardware block diagram of the image forming apparatus.

FIG. 4 is a hardware block diagram of the image forming apparatus 100.

The details of a controller 11, which controls the operation of the entire image forming apparatus 100, will be described with reference to FIG. 4.

As illustrated in FIG. 4, the image forming apparatus 100 includes the controller 11, which comprehensively controls the operation of the image forming apparatus 100, the display unit 12, the scanner unit 13, and the printer unit 14.

The controller 11 is communicably connected to the display unit 12, the scanner unit 13, and the printer unit 14. This controller 11 includes a central processing unit (CPU) 301, a random access memory (RAM) 302, a read only memory (ROM) 303, a power source control unit 304, an input/output interface (I/F) 305, and a local area network (LAN) controller 306. Then, the CPU 301, the RAM 302, the ROM 303, the power source control unit 304, the input/output I/F 305, and the LAN controller 306 are connected to a system bus 307.

Further, the controller 11 includes a hard disk drive (HDD) 308, an image processing unit 309, a scanner I/F 310, and a printer I/F 311. Then, the HDD 308, the image processing unit 309, the scanner I/F 310, and the printer I/F 311 are connected to an image bus 312.

The CPU 301 comprehensively controls access to currently connected various kinds of devices based on, for example, a control program stored in the ROM 303, and also comprehensively controls various kinds of processing performed by the controller 11.

The RAM 302 is a system work memory that allows the CPU 301 to operate. This RAM 302 is also a memory for temporarily storing image data. The ROM 303 stores a boot program of the apparatus and the like therein.

The power source control unit 304 controls power supply to each of the units of the image forming apparatus 100. The details of the power source control unit 304 will be described below. The input/output I/F 305 is an interface unit for connecting the system bus 307 and the display unit 12 to each other. This input/output I/F 305 receives image data to be displayed on the display unit 12 from the system bus 307 and outputs it to the display unit 12, and also outputs information input from the display unit 12 to the system bus 307. The LAN controller 306 transmits and receives information to and from an external apparatus 20 connected to a network 30.

The HDD 308 is a hard disk drive, and stores system software and image data therein. The image processing unit 309 functions to perform image processing, and performs image processing such as readout of the image data stored in the RAM 302, compression or decompression of image data of Joint Photographic Experts Group (JPEG), Joint Bi-level Image Experts Group (JBIG), or the like, and a color adjustment. The scanner I/F 310 is an interface unit for communicating with a scanner control unit 331 of the scanner unit 13. The printer I/F 311 is an interface unit for communicating with a printer control unit 341 of the printer unit 14. The image bus 312 is a transmission path for exchanging image data, and is formed by a bus such as a Peripheral Component Interconnect (PCI) bus or an Institute of Electrical and Electronics Engineers (IEEE) 1394 bus.

The CPU 301 transmits the image data to the display unit 12 via the system bus 307, and the display unit 12 displays this image data on the LCD 351. The user input from the touch panel 352 and the numerical keypad unit 353 is converted into digital data by a microcomputer 355, and is transmitted to the CPU 301 via the system bus 307. Further, when the user inserts the ID card into the card reader 354, the microcomputer 355 reads out data in the ID card and transmits this data to the CPU 301. The ID card may be configured in such a manner that the user touches the card reader 354 with it or holds it close to the card reader 354 instead of inserting it into the card reader 354.

The scanner unit 13 optically reads an image from the document and generates image data. The scanner unit 13 includes the scanner control unit 331, a scanner driving unit 332, and an opening/closing sensor 333. The scanner driving unit 332 includes a driving unit for moving a reading head that reads the document, a driving unit for conveying the document to a reading position, and the like.

The scanner control unit 331 controls the operation of the scanner driving unit 332. The scanner control unit 331 receives, via communication with the CPU 301, setting information set by the user when scanner processing is performed, and controls the operation of the scanner driving unit 332 based on this setting information. The scanner driving unit 332 has an automatic document feeder (hereinafter abbreviated as ADF) function for automatically conveying the sheet to be read, and can be opened from and closed to a glass serving as an image reading surface. The scanner control unit 331 detects opening/closing of the ADF unit by the opening/closing sensor 333.

The printer unit 14 forms an image on a recording medium (a sheet) according to the electrophotographic method. This printer unit 14 includes the printer control unit 341 and a printer driving unit 342. Further, a front door opening/closing sensor 343, a right door opening/closing sensor 344, an opening/closing sensor 345 for a sheet feeding tray 1, and an opening/closing sensor 346 for a sheet feeding tray 2 are connected to the printer control unit 341, and the printer control unit 341 has a function of detecting opening/closing of each unit of the printer unit 14.

The printer driving unit 342 includes a motor that rotates a non-illustrated photosensitive drum, a mechanism unit for pressing a fixing device, a heater, and the like. The printer control unit 341 controls the operation of the printer driving unit 342. The printer control unit 341 receives, via communication with the CPU 301, setting information set by the user when print processing is performed and controls the operation of the printer driving unit 342 based on this setting information.

Figure 5:
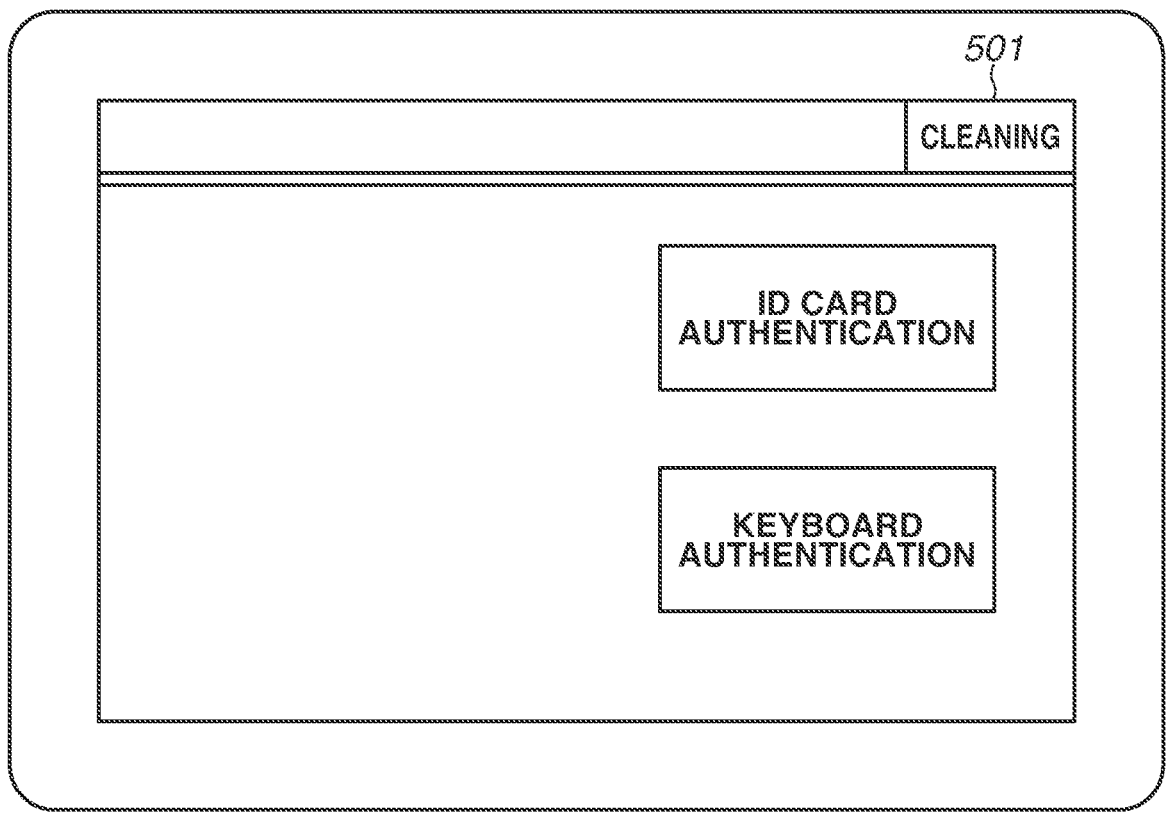
FIG. 5 illustrates an example of an initial screen for personal authentication.

FIG. 5 illustrates an example of an initial screen displayed on the LCD 351 in a case where the image forming apparatus 100 is set to require personal authentication to use the apparatus after the image forming apparatus 100 is powered on.

In FIG. 5, the user moves close to the image forming apparatus 100 and selects and touches a method displayed on the display unit 12. If the user selects an ID card authentication method and inserts the ID card into the card reader 354, the controller 11 of the image forming apparatus 100 reads out information written in the ID card, such as a user ID and a password. The controller 11 checks whether the user is registered by comparing the read information with a list stored in the HDD 308 (user authentication). If the user is authenticated, the screen on the LCD 351 is switched as indicated by an example illustrated in FIG. 6. If a cleaning button 501 is selected in FIG. 5, a screen illustrated in FIG. 7 is displayed. FIG. 7 will be described below.

Figure 6:
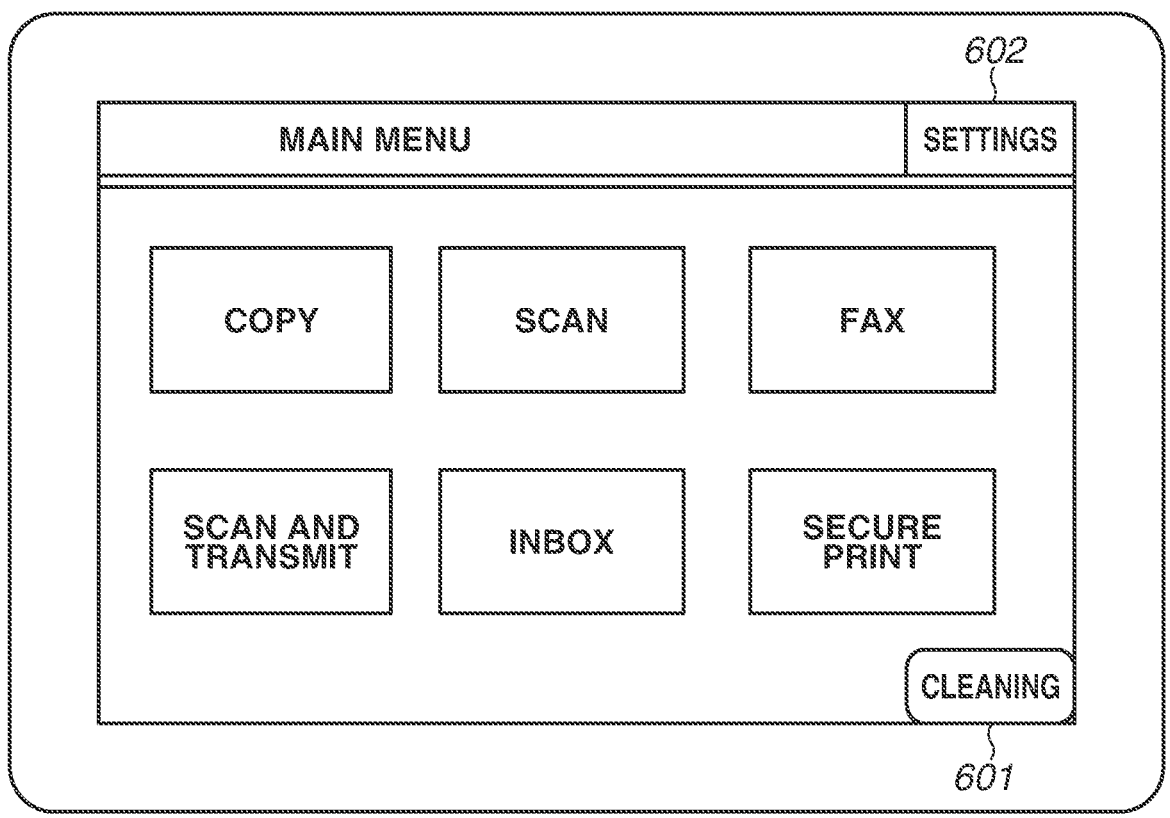
FIG. 6 illustrates an example of a menu screen as an initial screen.
Figure 7:
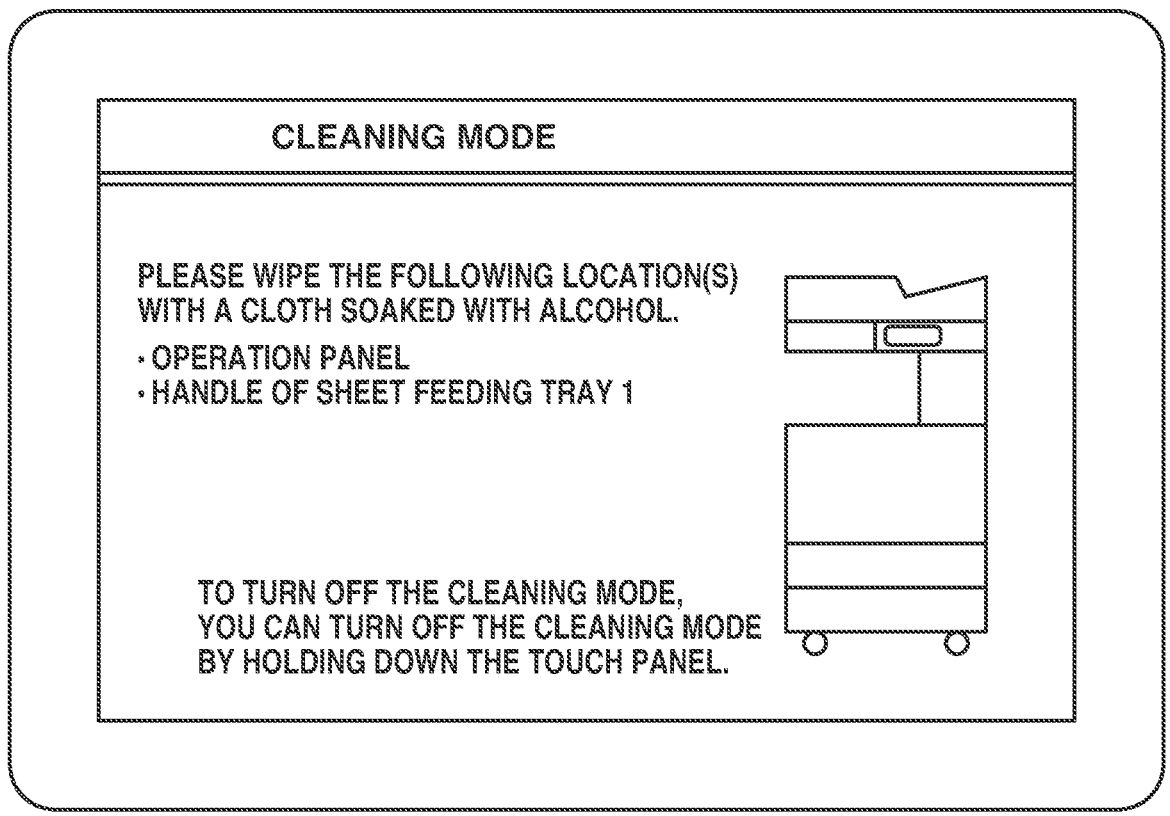
FIG. 7 illustrates an example of a display screen when the image forming apparatus enters a cleaning mode.

FIG. 6 is an example of a menu screen normally displayed on the LCD 351 after the personal authentication or in a case where the image forming apparatus 100 does not conduct the personal authentication. The user retrieves a further detailed setting screen and uses the image forming apparatus 100 by selecting and touching a function that the user wants to use from a main menu illustrated in FIG. 6.

Figure 12:
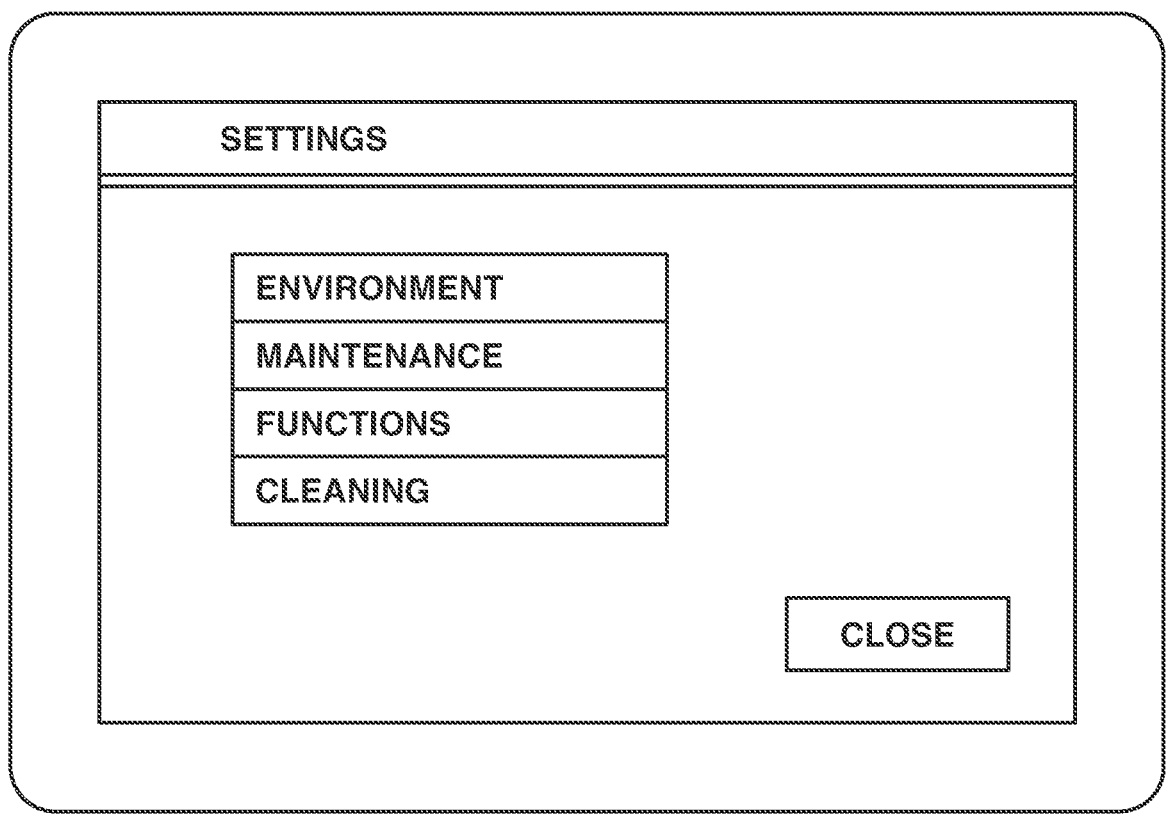
FIG. 12 illustrates a screen example of a setting screen.

The user can retrieve a setting screen illustrated in FIG. 12 and configure various kinds of functional settings by touching a setting button 602 at the upper right on the main menu screen illustrated in FIG. 6.

Figure 13:
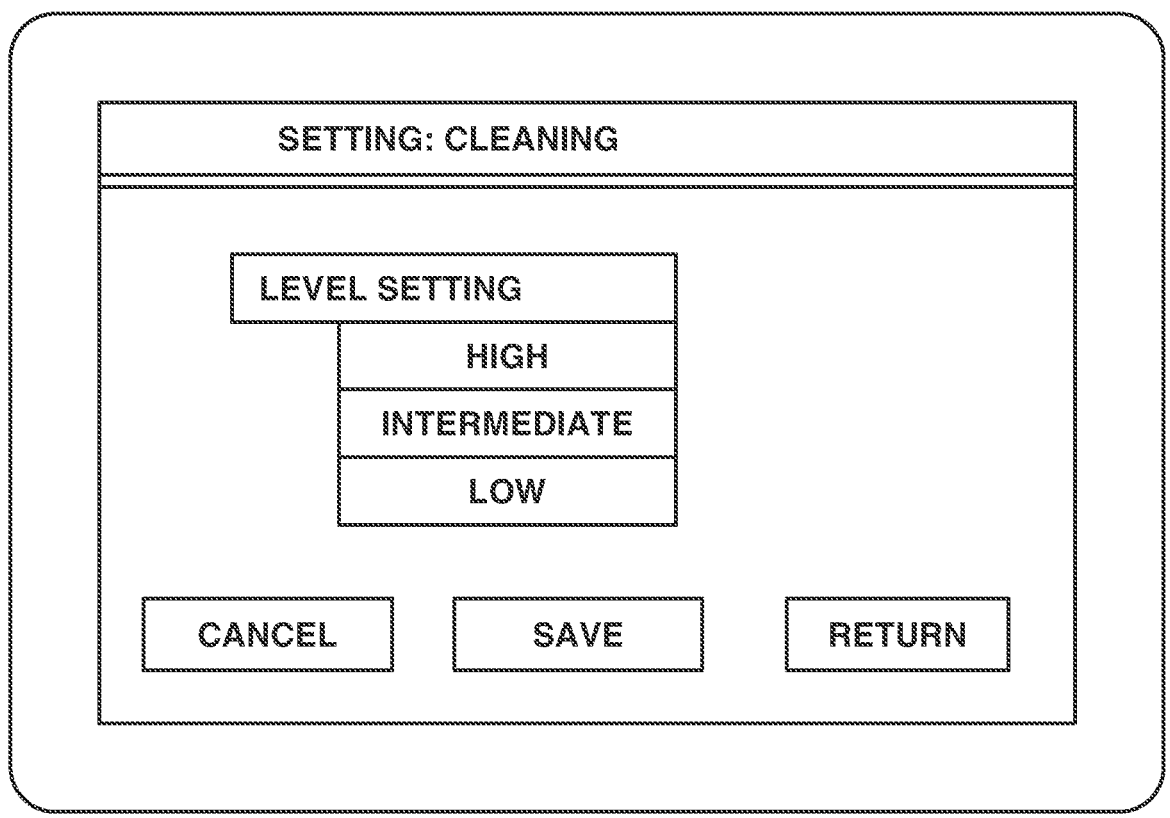
FIG. 13 illustrates an example of a screen for setting the level of the cleaning mode.

If the user presses the setting button 602 and selects a cleaning setting in FIG. 12, a screen illustrated in FIG. 13 is opened on which a level (priority) setting can be selected. This screen allows the user to select high, intermediate, and low levels by way of example. The setting information is stored into the RAM 302 when the level is selected and the cleaning level is changed, and is recorded into the HDD 308 when a save button is further pressed. If the save button is pressed without the level selected, the setting information in the HDD 308 is not changed.

If a cleaning button 601 is selected in FIG. 6, the screen illustrated in FIG. 7 is displayed on the LCD 351. FIG. 7 illustrates an example of the screen displayed on the LCD 351 when the image forming apparatus 100 enters the cleaning mode. The screen illustrated in FIG. 7 can issue, for example, a notification prompting disinfection to the user and a notification indicating the name of the member desired to be disinfected. The notification prompting disinfection is, for example, a notification instructing the user to wipe the member with an object (a cloth, paper, a disposable antiseptic wipe, or the like) soaked with disinfectant liquid. This notification may include a notification instructing the user not to directly apply the disinfectant liquid to the LCD 351 to prevent a failure in the apparatus. A location that the user prior to the user currently using the image forming apparatus 100 may have touched is displayed as the location desired to be disinfected. The details thereof will be described below. A notification unit that issues the notification prompting disinfection has been described and will be described citing the display using the display unit 12 as an example thereof herein. However, if the image forming apparatus 100 includes an audio output unit that issues an audio output in addition to the display unit 12, the notification unit may be the audio output unit. In the case where the notification unit is the audio output unit, the user is notified via an audio output.

In FIG. 7, the sensor of the touch panel 352 is turned off or a signal received from the sensor of the touch panel 352 is ignored so as not to cause an erroneous operation when the user wipes the screen with a cloth soaked with disinfectant liquid. Then, when the touch panel 352 receives a predetermined operation, the cleaning mode is ended. The predetermined operation is, for example, holding down the touch panel 352, holding down a key in the numerical keypad unit 353, or the like. The disinfectant liquid may be any disinfectant liquid capable of deactivating a virus, such as alcohol, a hypochlorous acid solution, and ethanol.

Further, in the case where the image forming apparatus 100 can collaborate with a mobile terminal, the screen of the cleaning mode may be displayed on the mobile terminal. In this case, the image forming apparatus 100 transmits information to be displayed on the screen to the mobile terminal via the above-described communication.

Further, the notification has been described citing the screen display illustrated in FIG. 7 as an example thereof, but the image forming apparatus 100 may be configured to notify the user via an audio output. In this case, the image forming apparatus 100 may notify the user via an audio output, or may be connected to a smart speaker and transmit information to the smart speaker and cause the smart speaker to notify the user via an audio output.

Referring back to FIG. 13, the setting level regarding the cleaning function will be further described.

FIGS. 14 to 16 illustrate tables indicating operation histories when the image forming apparatus 100 operates with different level settings (control settings), respectively. FIG. 14 illustrates the operation history when the cleaning level is low, FIG. 15 illustrates the operation history when the cleaning level is high, and FIG. 16 illustrates the operation history when the cleaning level is intermediate. Each row in the operation history indicates an operation history recorded by the CPU 301, and is numbered on the left side of the table for the sake of the description.

First, the operation history when the cleaning level is low, which is illustrated in FIG. 14, will be described. When the cleaning level is low, the image forming apparatus 100 enters the cleaning mode if the user presses the cleaning key.

The CPU 301, which is in operation with the initial screen illustrated in FIG. 5, records that the login method is selected, in an operation example 1-1. The LCD 351 is switched to the main menu display illustrated in FIG. 6 in reaction to the fact that a user A is authenticated, and the CPU 301 records that the user A touches a copy key on the touch panel 352 and presses the numerical keypad 353, in an operation example 1-2 and an operation example 1-3, respectively.

When the execution of the job is ended and the user A logs out, the CPU 301 returns the LCD 351 to the initial screen.

The CPU 301 stores that the next user selects the login method, in an operation example 1-4. The CPU 301 records that the login user B touches a scan and transmit key, in an operation example 1-5, and returns the LCD 351 to the initial screen when the execution of the job is ended and the user B logs out.

The CPU 301 records that the cleaning key 501 on the initial screen illustrated in FIG. 5 is pressed and the image forming apparatus 100 enters the cleaning mode, in an operation example 1-6. The CPU 301 records that the login method is selected, in an operation example 1-7. Then, the CPU 301 records that a user C touches the touch panel 352, presses the numerical keypad unit 353, and opens and closes the sheet feeding tray 1 along with a copy operation, in operation examples 1-8 to 1-10, respectively.

Next, the operation history when the cleaning level is high, which is illustrated in FIG. 15, will be described.

When the cleaning level is high, the CPU 301 displays the cleaning screen after a user logs in even if this login user is the same as the user who has logged in previously.

In an operation example 2-1, the CPU 301 displays the login selection screen illustrated in FIG. 5 on the LCD 351, and records that the login key is touched according to the fact that the user A logs in.

In an operation example 2-2, the CPU 301 displays the cleaning mode screen, and records that the user A touches the touch panel 352 when the user A cleans the image forming apparatus 100 and turns off the cleaning mode. Next, the CPU 301 records that the user A touches the copy key on the touch panel 352, in an operation example 2-3 and records that the user A further presses the numerical keypad 353, in an operation example 2-4. The screen returns to the login selection screen illustrated in FIG. 5 according to the fact that the user A logs out. The logout may be a logout due to time-out after the job is ended without the user logging out. The same also applies to the following operation examples.

In an operation example 2-5, the user A, which is the same as the previous login user, logs in after a while. According thereto, the CPU 301 records that the login key is touched by the user A. In an operation example 2-6, the CPU 301 displays the cleaning mode screen on the LCD 351 in reaction to the fact that the user A logs in. Then, when the user A cleans the image forming apparatus 100 and turns off the cleaning mode, and the CPU 301 records that the user A touches the touch panel 352.

The CPU 301 records that the user A touches the scan key in FIG. 6 that is displayed on the touch panel 352, in an operation example 2-7. The CPU 301 displays the login selection screen on the LCD 351 according to the fact that the execution of the job is ended and the user A logs out.

In an operation example 2-8, a user C, which is a user different from the previous login user, logs in. According thereto, the CPU 301 records that the login key is touched by the user C. In an operation example 2-9, the CPU 301 displays the cleaning mode screen on the LCD 351 in reaction to the fact that the user C logs in. Then, when the user C cleans the image forming apparatus 100 and turns off the cleaning mode, the CPU 301 records that the user C touches the touch panel 352. The CPU 301 records that the user C touches the copy key in FIG. 6 that is displayed on the touch panel 352 and opens and closes the sheet feeding tray 1, in an operation example 2-10 and an operation example 2-11, respectively.

The cleaning mode screen is displayed after the user logs in in FIG. 15, but the cleaning mode screen may be displayed before the user logs in. In this case, the operation examples 2-1 and 2-2 are interchanged, the operation examples 2-5 and 2-6 are interchanged, and the operation examples 2-8 and 2-9 are interchanged in FIG. 15.

Next, the operation history when the cleaning level is intermediate, which is illustrated in FIG. 16, will be described. When the cleaning level is intermediate, the CPU 301 does not display the cleaning screen after a user logs in if this login user is the same as the user who has logged in previously. In other words, the CPU 301 determines whether the user is changed and enters the cleaning mode if the user is changed, when the cleaning level is intermediate.

The CPU 301 displays the login selection screen illustrated in FIG. 5 on the LCD 351. In an operation example 3-1, the CPU 301 records that the login key is touched according to the fact that the user A logs in. Next, in an operation example 3-2, the CPU 301 switches the display on the LCD 351 to the cleaning mode screen illustrated in FIG. 7, and records that the user A touches the touch panel 352 when the cleaning mode is turned off.

The CPU 301 records that the user A touches the copy key on the touch panel 352, in an operation example 3-3 and records that the user A further presses the numerical keypad 353, in an operation example 3-4. When the user A logs out, the screen returns to the login selection screen.

In an operation example 3-5, the CPU 301 displays the login selection screen illustrated in FIG. 5 on the LCD 351. In the operation example 3-5, the CPU 301 records that the login key is touched according to the fact that the user A logs in. In the operation example 3-5, the same user A logs in again, and therefore the image forming apparatus 100 does not transition to the cleaning mode at this time.

The CPU 301 records that the user A touches the copy key on the touch panel 352, in an operation example 3-6, and next records that the user A touches the scan and transmit key on the touch panel 352, in an operation example 3-7. When the user A logs out, the screen returns to the login selection screen.

In an operation example 3-8, the CPU 301 records that the login key is touched according to the fact that the user C, who is different from the previous login user, logs in. Next, in an operation example 3-9, the CPU 301 switches the display on the LCD 351 to the cleaning mode screen illustrated in FIG. 7, and records that the user C touches the touch panel 352 when the cleaning mode is turned off. Then, in operation examples 3-10 and 3-11, the CPU 301 records that the user C touches the copy key on the touch panel 352 and opens and closes the sheet feeding tray 1, respectively.

In the following description, the operations will be described according to the flows illustrated in FIGS. 8 to 11.

Figure 8:
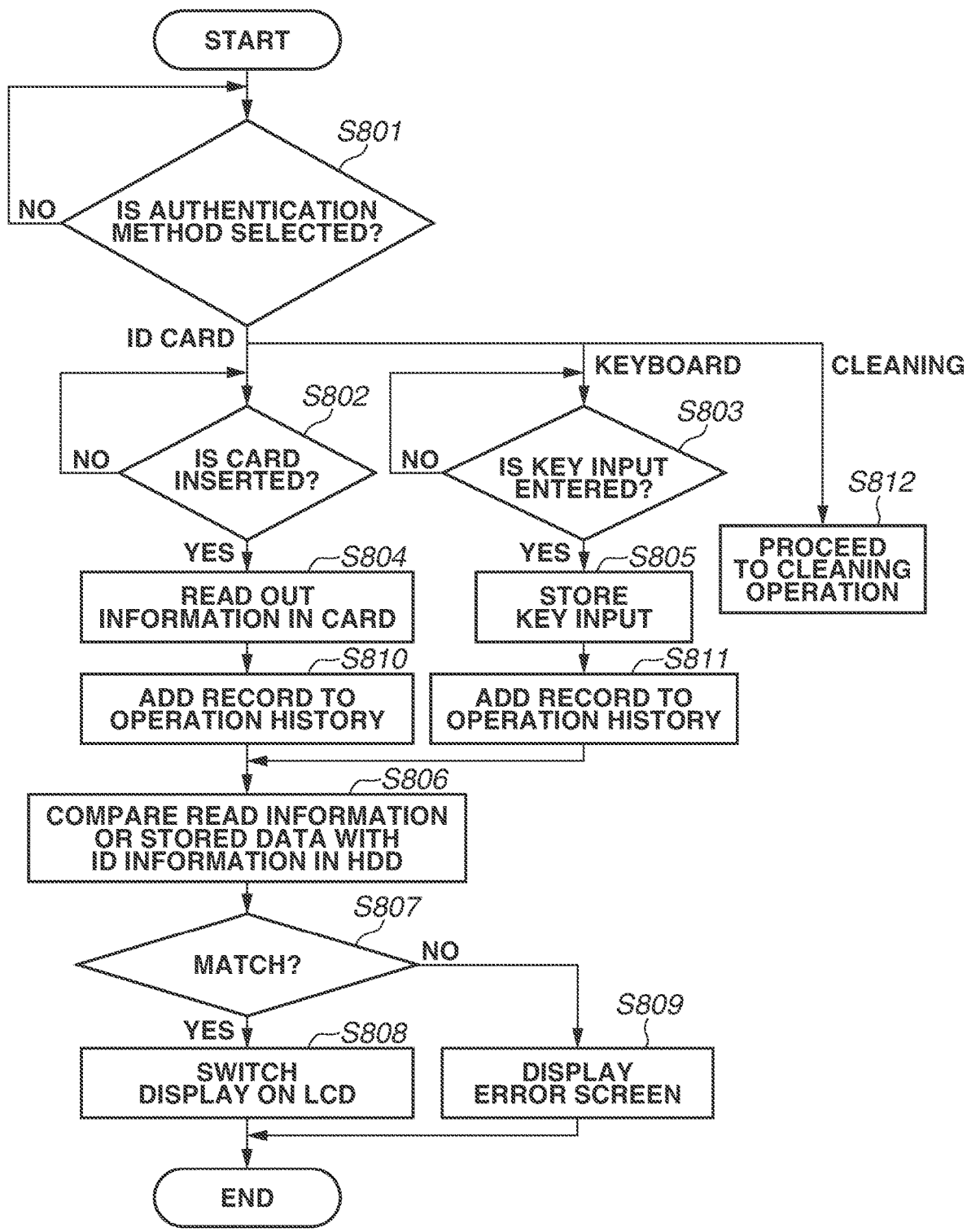
FIG. 8 is a flowchart of a user authentication operation.

FIG. 8 is a flowchart for illustrating the user authentication operation.

In step S801, the CPU 301 waits for a user's touch input on the authentication method selection screen displayed on the LCD 351. If the ID card authentication key is touched by the user (ID CARD in step S801), the processing proceeds to step S802. If the keyboard authentication key is touched (KEYBOARD in step S801), the processing proceeds to step S803. If the cleaning key 501 is touched (CLEANING in step S801), the processing proceeds to step S812. If no input is entered (NO in step S801), the processing returns to step S801.

In step S802, the CPU 301 detects whether the card for the authentication is inserted into the card reader 354 by the user. If the card is inserted (YES in step S802), the processing proceeds to step S804. If the card is not inserted (NO in step S802), the processing returns to step S802.

In step S804, the CPU 301 reads out the information in the ID card using the card reader 354. Then, the processing proceeds to step S810.

In step S810, the CPU 301 adds a record indicating that the login operation is performed using the IC card, to the operation history. Then, the processing proceeds to step S806.

In step S803, the CPU 301 detects whether an input is entered onto the numerical keypad 353 by the user. If a key input is detected (YES in step S803), the processing proceeds to step S805. If no key input is detected (NO in step S803), the processing returns to step S803. In step S805, the CPU 301 temporarily stores the data input by the user into the memory 302. Then, the processing proceeds to step S811. In step S811, the CPU 301 adds a record indicating that the login operation is performed using the key input, to the operation history. After step S811 is ended, the processing proceeds to step S806.

In step S806, the CPU 301 compares the ID information stored in the HDD 308 and the information read out in step S804 or the key input data temporarily stored in step S805. Then, the processing proceeds to step S807.

In step S807, the CPU 301 determines whether the compared pieces of information match each other as a result of the comparison in step S806. If they match each other (YES in step S807), the processing proceeds to step S808. If they do not match each other (NO in step S807), the processing proceeds to step S809.

In step S808, the CPU 301 switches the display on the LCD 351 to the default screen predetermined for each cleaning level.

In step S809, the CPU 301 displays an error on the LCD 351. In step S812, the CPU 301 proceeds to the cleaning operation, and displays the cleaning mode screen illustrated in FIG. 7.

Figure 9:
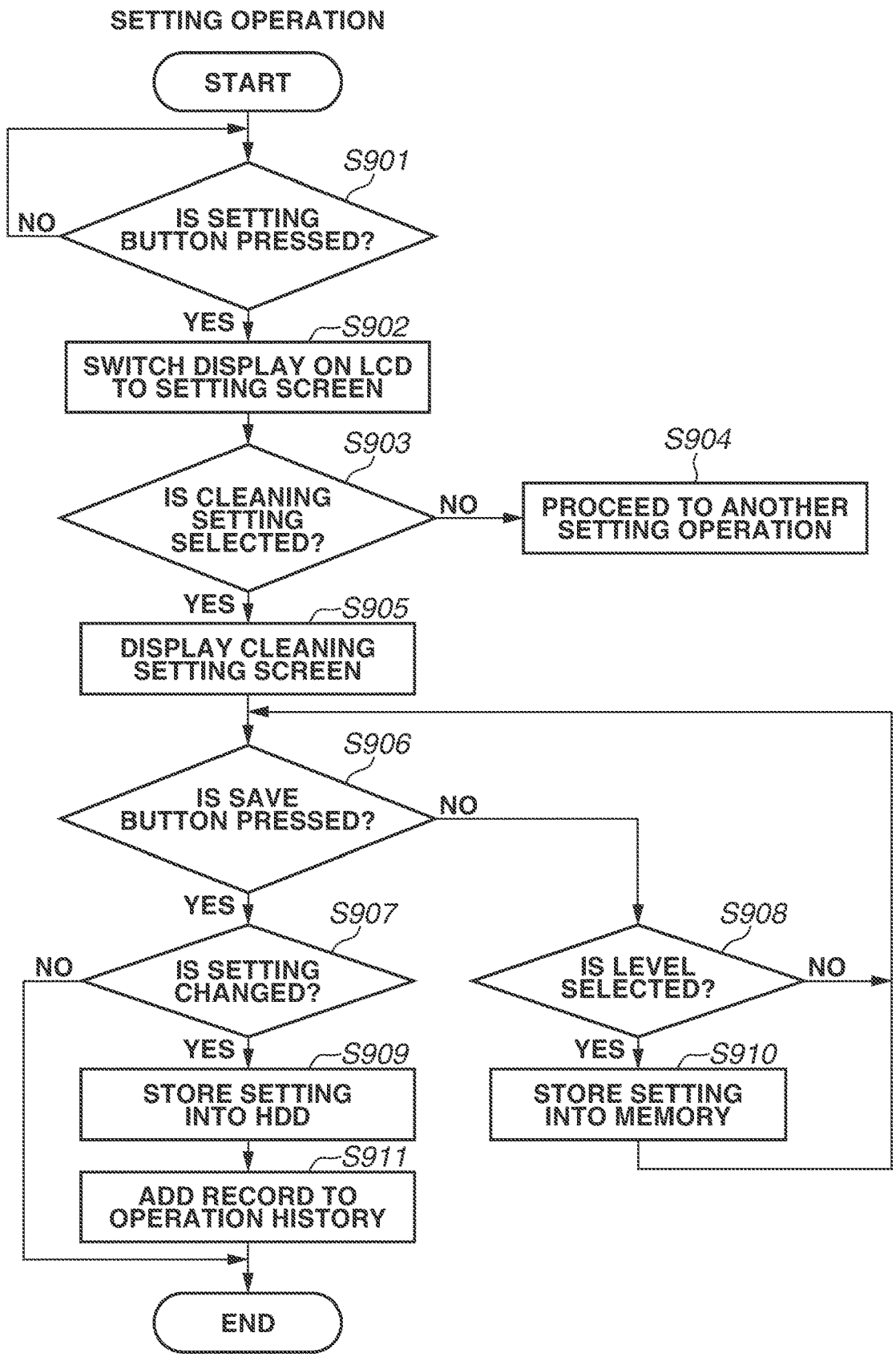
FIG. 9 is a flowchart of an operation of configuring a cleaning level setting.

FIG. 9 is a flowchart for illustrating an operation of configuring the cleaning level setting in the device settings. The screen illustrated in FIG. 13 serves as the setting screen.

In step S901, the CPU 301 detects whether the setting button 602 is selected on the touch panel 352 illustrated in FIG. 6. If the setting button 602 is selected (YES in step S901), the processing proceeds to step S902. If the setting button 602 is not selected (NO in step S901), the processing returns to step S901.

In step S902, the CPU 301 switches the display on the LCD 351 to the setting screen illustrated in FIG. 12. Then, the processing proceeds to step S903.

In step S903, the CPU 301 detects whether the cleaning setting key is selected on the touch panel 352. If the cleaning setting key is selected (YES in step S903), the processing proceeds to step S905. If a setting key or the like other than that is touched (NO in step S903), the processing proceeds to step S904.

In step S905, the CPU 301 switches the display on the LCD 351 to the cleaning setting screen illustrated in FIG. 13.

In step S906, the CPU 301 determines whether the save button is pressed on the touch panel 352. If the save button is pressed (YES in step S906), the processing proceeds to step S907. If not (NO in step S907), the processing proceeds to step S908.

In step S908, the CPU 301 determines whether the level of the cleaning mode is selected. If the level of the cleaning mode is selected (YES in step S908), the processing proceeds to step S910. If not (NO in step S908), the processing returns to step S906.

In step S910, the CPU 301 stores the selected level information of the cleaning mode into the RAM 302. Then, the processing proceeds to step S906.

In step S907, the CPU 301 determines whether the setting information of the cleaning mode is changed. If the setting is changed (YES in step S907), the processing proceeds to step S909. If the setting information is not changed (NO in step S907), the operation of configuring the cleaning level setting is ended.

In step S909, the CPU 301 stores the changed setting information into the HDD 308. After step S909 is ended, the processing proceeds to step S911. In step S911, the CPU 301 adds a record indicating that the setting operation is performed, to the operation history. After the addition is completed, the setting operation is ended.

Next, the operation according to the difference in the cleaning level will be described with reference to the flowchart illustrated in FIG. 10.

In step S1001, the CPU 301 starts initial processing after the image forming apparatus 100 is powered on.

In step S1002, the CPU 301 reads out the setting information of the cleaning level stored in the HDD 308. After step S1002 is ended, the processing proceeds to step S1020.

If the CPU 301 detects the user due to the fact that the user touches, for example, the touch panel 352 to log in in step S1020 (YES in step S1020), the processing proceeds to step S1003. If the user is not detected (NO in step S1020), the processing stays in step S1020.

In step S1003, the CPU 301 determines the cleaning level information read out in step S1002. If the cleaning level information is low (LOW in step S1003), the processing proceeds to step S1004. If the cleaning level information is intermediate (INTERMEDIATE in step S1003), the processing proceeds to step S1008. If the cleaning level information is high (HIGH in step S1003), the processing proceeds to step S1007.

In step S1004, the CPU 301 proceeds to the authentication operation in step S801. After the user authentication operation illustrated in FIG. 8 is ended, the processing proceeds to step S1005. In step S1005, the CPU 301 displays the menu screen on the LCD 351 because the user authentication is ended. After step S1005 is ended, the processing proceeds to step S1006.

In step S1008, the CPU 301 proceeds to the authentication operation in step S801. In step S1009, the CPU 301 determines whether the authenticated user is the same as the user that has logged in immediately before this time. If the user is the same (NO in step S1009), the processing proceeds to step S1005. If the user is different (YES in step S1009), the processing proceeds to step S1010.

In step S1007, the CPU 301 proceeds to the authentication operation in step S801. After the authentication operation is completed, the processing proceeds to step S1010.

In step S1010, the CPU 301 proceeds to the cleaning mode operation in step S1101. In step S1011, the CPU 301 determines whether the cleaning mode is turned off. If the cleaning mode is turned off (YES in step S1011), the processing proceeds to step S1006. If the cleaning mode is not turned off (NO in step S1011), the processing stays in step S1011. If the cleaning mode is turned off (YES in step S1011), the processing proceeds to step S1006.

In step S1006, the CPU 301 determines whether the user enters a touch input to select an operation on the touch panel 352 from the menu screen displayed on the LCD 351. If a selection is made (YES in step S1006), the processing proceeds to any of steps S1012 to S1016 corresponding to the selected operation. If no selection is made (NO in step S1006), the processing stays in step S1006.

If the copy is selected, the processing proceeds to step S1012. If the scan is selected, the processing proceeds to step S1013. If the FAX operation is selected, the processing proceeds to step S1014. If the scan and transmit operation is selected, the processing proceeds to step S1015. If the secure print operation is selected, the processing proceeds to step S1016. After each operation is ended, the processing proceeds to step S1017.

In step S1017, the CPU 301 adds the performed operation among steps S1012 to S1016 to the operation history. Then, the processing proceeds to step S1018. Further, in step S1018, the CPU 301 records information about a change in an input from each sensor in the apparatus that is detected along with the performed operation among steps S1012 to S1016. After step S1018 is ended, the processing proceeds to step S1019.

In step S1019, the CPU 301 determines whether the user logs out. If the user logs out (YES in step S1019), the processing proceeds to step S1020. If the user does not log out (NO in step S1019), the processing proceeds to step S1006.

Figure 10:
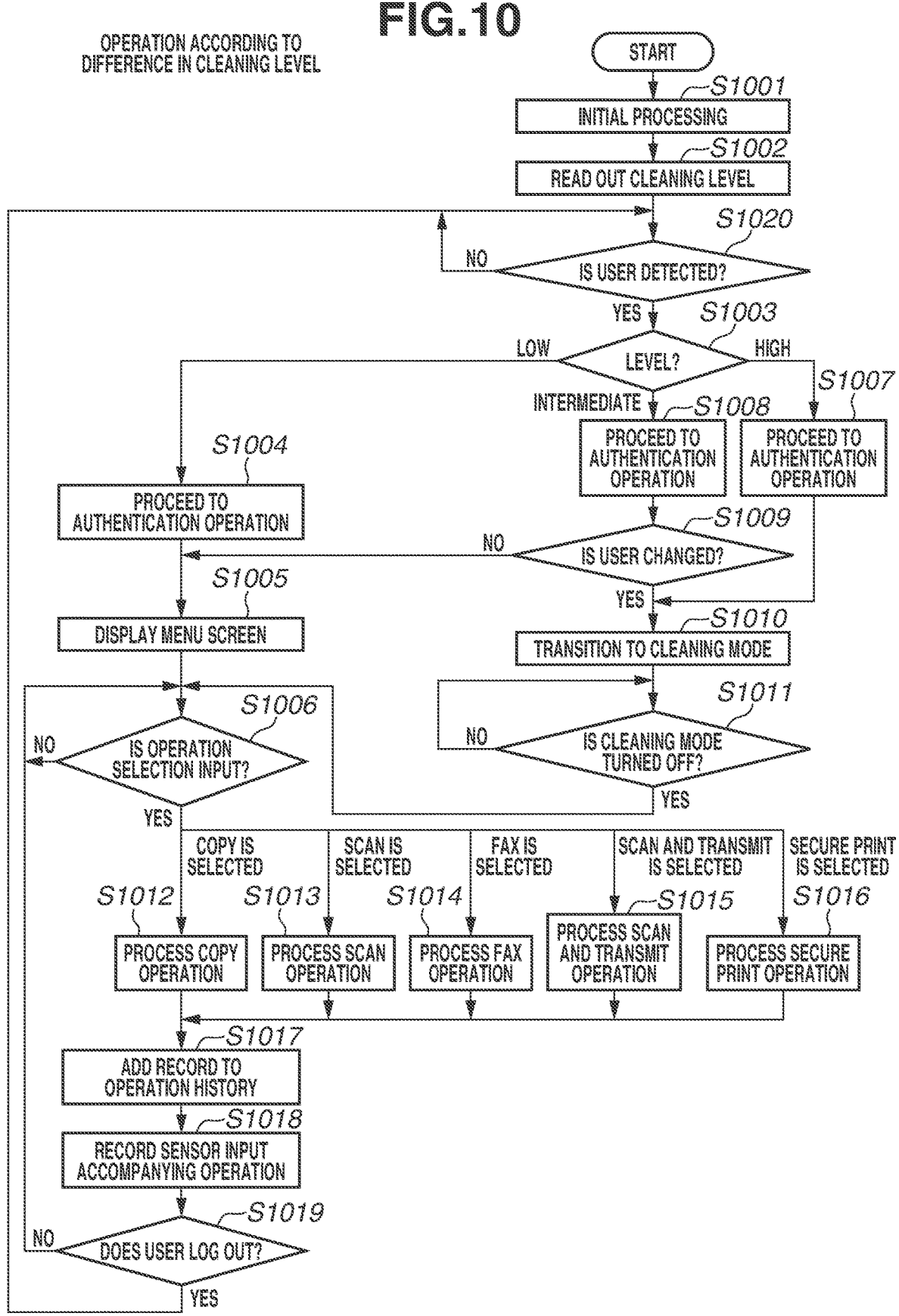
FIG. 10 is a flowchart of an operation according to a difference in the cleaning level.

The image forming apparatus 100 determines where the user touches when performing the operation using a change in the sensor mounted on each portion of the MFP in FIG. 10, but is not limited thereto. For example, the image forming apparatus 100 may be configured to set in advance a location that the user may touch in association with each of the operations in steps S1012 to S1016. In this case, desirably, the image forming apparatus 100 is configured to store a table in which each operation and a location that the user may touch are associated with each other in advance. For example, when carrying out scanning, the user may touch the platen and the automatic document feeder, may touch a handle for opening and closing them, and may also touch the sheet discharge tray (the finisher) of the scanned document. In the print operation, the user may touch the sheet feeding tray for opening and closing it, and may touch the sheet discharge tray for extracting the discharged sheet. The image forming apparatus 100 sets an operation and a location that the user may touch in each operation in this manner in association with each other. Alternatively, the image forming apparatus 100 may be configured to combine the detection using the sensor and the above-described contact prediction.

Figure 11:
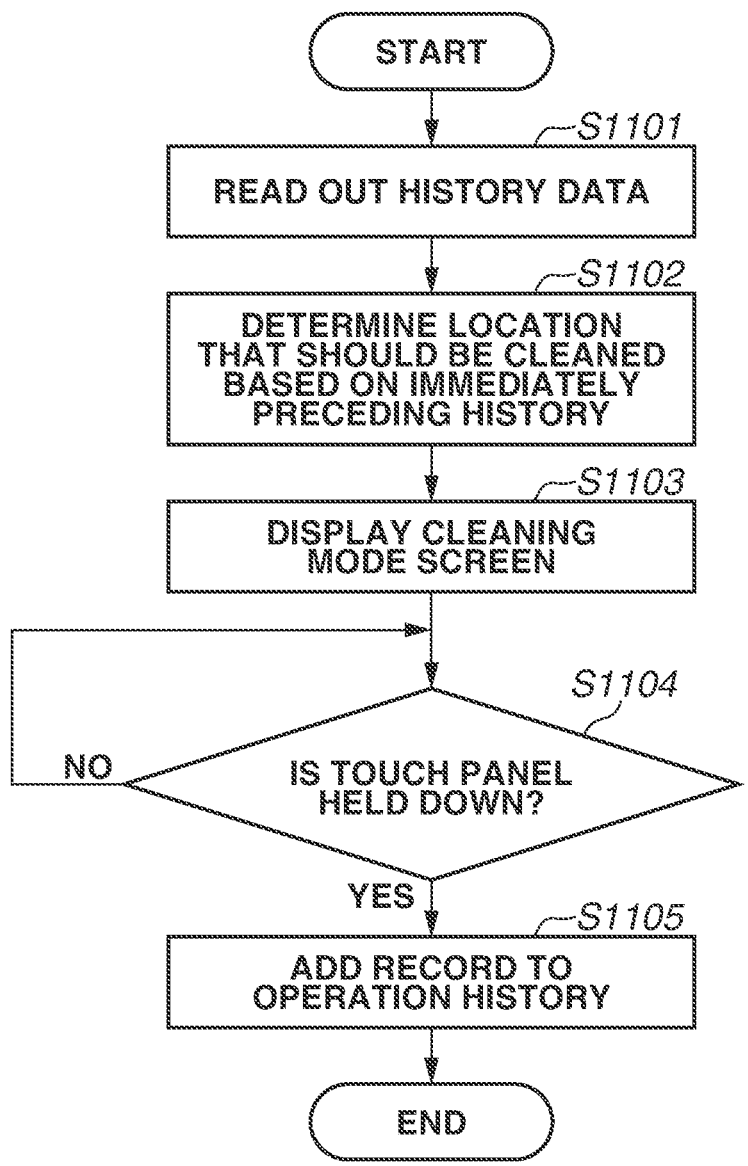
FIG. 11 illustrates a flowchart of an operation in the cleaning mode.

FIG. 11 is a flowchart for illustrating the operation in the cleaning mode.

In step S1101, the CPU 301 reads out the operation history (FIGS. 14 to 16) stored in the HDD 308.

In step S1102, the CPU 301 extracts a location touched by the user on the image forming apparatus 100 but not cleaned yet based on the immediately preceding history information. The immediately preceding history information refers to history information after the image forming apparatus 100 has been cleaned due to the cleaning mode last time. This will be described citing FIG. 15 as an example. For example, when the cleaning mode is in operation in the operation example 2-6, the operation example 2-2 corresponds to the cleaning mode performed last time. Therefore, the operation history information indicating the input detection and the copy operation in the operation example 2-2 to the operation example 2-5 is used as the immediately preceding history information.

In step S1103, the CPU 301 displays information about the location extracted in step S1102 by adding it to the LCD 351, like the screen example illustrated in FIG. 7. In step S1104, the CPU 301 detects whether the user holds down the same position on the touch panel 352. If the user does not hold down the same position (NO in step S1104), the processing returns to step S1104, determining that the cleaning is still ongoing. If the CPU 301 detects that the user holds down the same position in step S1104 (YES in step S1104), the cleaning mode is ended, and the processing proceeds to step S1105. In step S1105, the CPU 301 adds a record indicating that the image forming apparatus 100 transitions to the cleaning mode and ends the cleaning mode, to the operation history. After step S1105 is ended, the flow ends.

The method for turning off the cleaning mode in step S1104 has been described citing the example in which the cleaning mode is turned off when the CPU 301 detects that the user holds down the touch panel 352, and the time length for which the user should keep holding down the touch panel 352 may be any length enough to allow the operation to be distinguished from a touch accompanying the cleaning. For example, in a case where the criterion for the holding-down operation is set to 3 seconds, the information processing apparatus 100 can be prevented from transitioning from the cleaning mode to an unintended mode by displaying a countdown on the LCD 351 and making the user aware of it. Further, the method for turning off the cleaning mode is not limited to the holding-down operation, and similar beneficial effects can also be acquired by a method that sets the condition for turning off the cleaning mode to an operation of pressing the same location a predetermined number of times successively within a predetermined time, although this has not been described in the above-described exemplary embodiment.

Further, the image forming apparatus 100 has been described, purposefully indicating that, even when an openable/closable portion in the apparatus is opened/closed, the display on the LCD 351 during the cleaning mode does not react thereto. This is intended to prevent the user's cleaning from being interrupted when the door is unintentionally opened/closed along with the cleaning during the cleaning mode, although opening/closing the front door or the like causes the display on the LCD 351 to be changed in reaction thereto in a normal operation mode. This does not lead to any inconvenience by displaying the state of the above-described door or the like when the image forming apparatus 100 returns from the cleaning mode to the normal operation mode.

In the above-described manner, the user using the MFP can understand which configuration in the MFP other than the touch panel should be disinfected when the touch panel is disabled. As a result, the user can effectively sterilize or sanitize the MFP by cleaning.

Other Embodiments

Embodiment(s) of the disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2020-151318, filed Sep. 9, 2020, which is hereby incorporated by reference herein in its entirety.

What is claimed is:

1. An information processing apparatus comprising:
   a notification interface (IF) configured to notify a user of information; and
   a controller configured to identify a unit that the user has touched when the user has operated the information processing apparatus among a plurality of units included in the information processing apparatus,
   wherein the notification IF can notify the user of first information indicating the identified unit that the user has touched and second information regarding disinfection of the identified unit that the user has touched.

2. The information processing apparatus according to claim 1, wherein the notification IF includes a touch panel configured to receive an instruction to transition to a mode in which the first information and the second information are notified, and
   wherein the notification IF notifies the user of the first information and the second information according to the fact that the touch panel receives the instruction to transition to the mode.

3. The information processing apparatus according to claim 2, wherein, after the information processing apparatus transitions to the mode, the notification IF is enabled to notify notifies the user of the first information and the second information that the user is not notified before the transition to the mode.

4. The information processing apparatus according to claim 2, wherein based on the fact that the controller identifies that the touch panel receives the operation performed by the user, the notification IF is enabled to notify information indicating the identified touch panel as the first information.

5. The information processing apparatus according to claim 4, wherein the notification IF includes a display capable of displaying the first information and the second information, and wherein the touch panel does not receive an operation performed by the user except for a predetermined operation according to the fact that the notification is displayed on the display.

6. The information processing apparatus according to claim 5, wherein the predetermined operation is holding down the touch panel, and wherein, after the user holds down the touch panel, the display transitions from a screen displaying the notification to a screen capable of receiving an operation performed by the user.

7. The information processing apparatus according to claim 5, wherein the second information includes information for preventing the user from directly applying disinfectant liquid to the display.

8. The information processing apparatus according to claim 2, further comprising:
   a printer configured to print image data on a sheet; and
   a sheet feeding tray configured to hold the sheet,
   wherein the controller can identify that the sheet feeding tray is operated by the user by detecting that the sheet feeding tray is opened/closed, and
   wherein the notification IF is enabled to display information indicating the sheet feeding tray.

9. The information processing apparatus according to claim 1, further comprising an authentication interface (IF) configured to authenticate the user,
   wherein, in a state that the controller sets a first setting among a plurality of settings, the notification unit IF is enabled to notify the user of the first information and the second information before the authentication IF authenticates the user.

10. The information processing apparatus according to claim 9,
    wherein the notification IF includes a touch panel configured to receive an instruction to transition to a mode that causes the notification IF to issue the notification, wherein, in a state that the controller sets a second setting in which lower priority is placed on the notification of the first information and the second information than in the first setting, the notification IF is enabled to notify the user of the first information and the second information according to the fact that the instruction to transition to the mode is received.

11. The information processing apparatus according to claim 10, wherein, in a state that the controller sets a third setting in which priority of the mode is lower than in the second setting, the notification IF notifies the user of the first information and the second information according to a fact that the user is authenticated by the authentication IF and the authenticated user is different from a previous user, and does not notify the user of the first information and the second information according to the fact that the user is authenticated by the authentication IF and the authenticated user is the same as the previous user.

12. The information processing apparatus according to claim 1, further comprising a scanner configured to read a document and generate an image, wherein the scanner includes an opening/closing sensor, and wherein the controller identifies that the scanner is operated according to the fact that the opening/closing sensor detects that the scanner is opened/closed, and wherein the notification IF displays information indicating the scanner as the first information.

13. The information processing apparatus according to claim 1, wherein the controller can identify that a finisher connected to the information processing apparatus is operated by the user, and wherein the notification IF is enabled to notify information indicating the finisher as the first information.

14. The information processing apparatus according to claim 1, wherein the second information includes an instruction to wipe at least the identified unit with an object soaked with disinfectant liquid.

15. The information processing apparatus according to claim 1, wherein the first information is a graphic indicating at least a location of the identified unit.

16. The information processing apparatus according to claim 1, wherein the first information at least is a name of the identified unit.

17. The information processing apparatus according to claim 1, wherein the plurality of units includes respective sensors, and wherein the controller determines whether the user has touch a unit when the user has operated the information processing apparatus, based on results of detection by the sensors of the plurality of units.

18. A method for controlling an information processing apparatus, the information processing apparatus including a notification interface (IF) configured to notify a user of information, a controller, and a storage device, the method comprising:
    identifying a unit that the user has touched when the user has operated the information processing apparatus among a plurality of units included in the information processing apparatus; and notifying the user of first information indicating the identified unit that the user has touched and second information regarding disinfection of the identified unit that the user has touched.

19. A non-transitory computer-readable storage medium storing a program for causing a computer to execute a method for controlling an information processing apparatus, the information processing apparatus including a notification interface (IF) configured to notify a user of information, a controller, and a storage device, the method comprising:
   identifying a unit that the user has touched when the user has operated the information processing apparatus among a plurality of units included in the information processing apparatus; and
   notifying the user of first information indicating the identified unit that the user has touched and second information regarding disinfection of the identified unit that the user has touched.

* * * * *